United States Patent [19]

Lang, Jr. et al.

[11] Patent Number: 4,515,954

[45] Date of Patent: May 7, 1985

[54] METAL CHELATES OF ANTHRACENE-9,10-BIS-CARBONYLHYDRAZONES

[75] Inventors: Stanley A. Lang, Jr., Blauvelt; Keith C. Murdock, Pearl River, both of N.Y.

[73] Assignee: American Cyanamid Company, Stamford, Conn.

[21] Appl. No.: 500,225

[22] Filed: Jun. 6, 1983

Related U.S. Application Data

[63] Continuation-in-part of Ser. No. 295,946, Aug. 24, 1981, abandoned.

[51] Int. Cl.$^3$ ............................................ C07D 233/06
[52] U.S. Cl. ............................. 548/109; 544/4; 544/64; 544/225; 544/226; 546/2; 548/402; 549/10; 260/239 BC; 260/239 BE; 260/330.6; 260/429 C; 260/429 J; 260/429.9; 260/429.3; 260/438.1; 260/438.5 R; 260/439 R

[58] Field of Search ............... 542/415; 548/109, 402; 544/4, 64, 225, 226; 546/2; 260/429 J, 429.3, 429.9, 438.1, 438.5 R, 439 R, 429 C, 330.6, 239 BC, 239 BE; 549/10

[56] References Cited

U.S. PATENT DOCUMENTS 4,258,181  5/1981  Murdock et al. ................. 542/415
4,296,030 10/1981  Lang, Jr. et al. ................. 544/225

OTHER PUBLICATIONS

Gosalvez et al., Europ. J. Cancer, vol. 14, pp. 1185–1190 (1978).

Primary Examiner—Henry R. Jiles
Assistant Examiner—Bernard I. Dentz
Attorney, Agent, or Firm—Anne M. Rosenblum

[57] ABSTRACT

This disclosure describes metal chelates of anthracene-9,10-bis-carbonylhydrazones and derivatives thereof useful as antibacterial agents, for inhibiting the growth of transplanted mouse tumors, and for inducing the regression and/or palliation of leukemia and related cancers.

8 Claims, No Drawings

METAL CHELATES OF ANTHRACENE-9,10-BIS-CARBONYLHYDRAZONES

This application is a continuation-in-part of application Ser. No. 295,946, filed 8/24/81, now abandoned.

BACKGROUND OF THE INVENTION

1. Field of Invention

The present invention relates to novel metal chelates of anthracene-9,10-bis-carbonylhydrazones and their acid-addition and quaternary ammonium salts, to the use of such compounds as antibacterial agents, for inhibiting the growth of transplanted mouse tumors and for inducing the regression and/or palliation of leukemia and related cancers.

2. Description of the Prior Art

The applicants are not aware of any prior art patents or publications which, in their respective judgment, should be deemed to anticipate or render obvious the compounds and processes described and claimed herein. By way of background, U.S. Pat. No. 4,258,181 and M. Gosálvez, M. F. Blanco, C. Vivero, and F. Valkés, Europ. J. Cancer 14: 1185-90 (1978) are cited.

SUMMARY OF THE INVENTION

The instant invention relates to novel metal chelates of anthracene-9,10-bis-carbonylhydrazones which may be represented by the following general formula I:

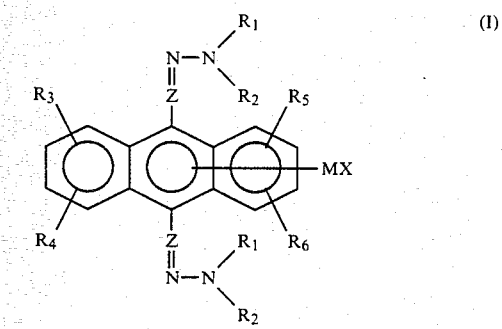

wherein Z is a trivalent moiety of the formulae:

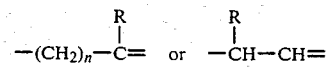

wherein n is 0, 1, 2 or 3 and R is hydrogen or alkyl ($C_1$–$C_4$); $R_1$ is hydrogen or alkyl ($C_1$–$C_4$); $R_2$ is hydrogen, alkyl ($C_1$–$C_4$) or a monovalent moiety of the formulae:

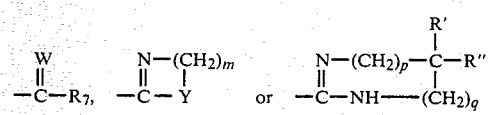

wherein m is 2, 3, 4 or 5, p is 1, 2 or 3, q is 0, 1 or 2; R' is hydrogen or alkyl ($C_1$–$C_4$); R" is hydrogen or alkyl ($C_1$–$C_4$); $R_7$ is alkyl ($C_1$–$C_4$), amino, anilino, hydrazino, alkylamino ($C_1$–$C_4$), dialkylamino wherein each alkyl group has up to 4 carbon atoms, α-phenethylamino, β-phenethylamino, pyrrolidino, piperidino, N-methylpiperazino or a moiety of the formula:

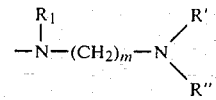

wherein m, $R_1$, R' and R" are as hereinbefore defined and the moiety —NR'R" may be pyrrolidino, piperidino, morpholino or N-methylpiperazino; W is oxo (O=), thioxo (S=) or imino (R'—N= wherein R' is as hereinbefore defined) and Y is oxy (—O—), thio (—S—), methylene (—CH₂—) or a divalent group of the formula:

wherein $R_8$ is hydrogen or alkyl ($C_1$–$C_4$); and $R_3$, $R_4$, $R_5$, and $R_6$ are each individually selected from the group consisting of hydrogen, halogen (F, Cl, Br, I), hydroxy, nitro, amino, sulfonamido, alkyl ($C_1$–$C_3$) and alkoxy ($C_1$–$C_3$); M is platinum, copper, iron, zirconium, cobalt, chromium or zinc; X is sulfate, halogen (F, Cl, Br, I), nitrate, dicyclopentadienyl or amine ligand; and the nontoxic pharmaceutically acceptable acid-addition and quaternary ammonium salts thereof.

The hydrazono substituents pendant from the anthracene-9,10-carbonyl nuclei may be the same or different and may be in the syn or anti forms. These compounds form chelates with metal atoms such as platinum, copper, iron, zirconium, cobalt, chromium, zinc, and the like which are the essence of this invention.

A preferred embodiment of the present invention consists of metal chelates of compounds which may be represented by the following structural formula II:

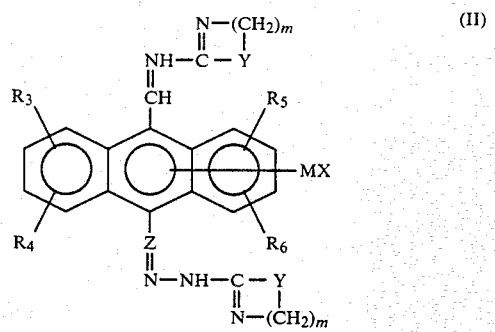

wherein $R_3$, $R_4$, $R_5$, $R_6$, Y and m are as hereinabove described, M is a chelating agent such as iron, platinum, copper, zinc, chromium, zirconium, cobalt or palladium and X is the corresponding counter ion such as halogen, sulfate, nitrate, dicyclopentadienyl or amine ligand.

DETAILED DESCRIPTION OF THE INVENTION

The novel chelates of the present invention are obtainable as amorphous materials having characteristic absorption spectra. The organic chelated bases of this invention form nontoxic acid-addition and quaternary ammonium salts with a variety of nontoxic pharmaceutically acceptable organic and inorganic salt-forming reagents. For purposes of this invention the chelated free bases are equivalent to their nontoxic acid-addition salts.

The novel compounds of the present invention are useful as antimicrobial agents and possess broad-spectrum anti-bacterial activity in vitro against a variety of standard laboratory microorganisms as determined by the standard agar well diffusion assay. In this assay, the minimal inhibitory concentration (MIC) was determined by using twofold dilutions of the compound in nutrient agar. One ml of each dilution was placed in a sterile Petri dish; 9 ml of nutrient agar was added to each dish. Five-hour cultures of the indicated organism in Trypticase Soy Broth were diluted $10^{-2}$ in nutrient broth. This dilution of each culture was transferred to the surface of the plates by using a Steers replicating device. After incubation at 35° C. for 18 hours, the MIC was recorded as the lowest concentration of the compound which completely inhibits the macroscopic growth of each organism. The MIC of typical compounds of the present invention against the indicated organisms are set forth in Table I below.

TABLE I

| Organism | Minimal Inhibitory Conc. (mcg/ml) | | | |
|---|---|---|---|---|
| | (1) | (2) | (3) | (4) |
| Enterococcus OSU-75-1 | 16 | 64 | 128 | 64 |
| Enterococcus SM 77-15 | 8 | 32 | 64 | 64 |
| Staphylococcus aureus SSC 70-18B | 16 | 64 | 64 | 64 |
| Micrococcus luteus PCI 1001 | 16 | 32 | 64 | 32 |
| Staphylococcus aureus SMITH | 16 | 32 | 64 | 32 |
| Staphylococcus aureus ATCC 25923 | 64 | 128 | 512 | 128 |

(1) Bis (2-imidazolin-2-ylhydrazone) of 9,10-anthracenedicarboxaldehyde, dichloride, bis (cuprous chloride chelate)
(2) Bis (2-imidazolin-2-ylhydrazone) of 9,10-anthracenedicarboxaldehyde, tetrachloride, bis (dicyclopentadienyl zirconium chelate)
(3) Bis (2-imidazolin-2-ylhydrazone) of 9,10-anthracenedicarboxaldehyde, tetrachloride, bis (chromic chloride chelate)
(4) Bis (2-imidazolin-2-ylhydrazone) of 9,10-anthracenedicarboxaldehyde, trisulfate, tris (zinc chelate).

The novel chelated compounds of the present invention possess the property of inhibiting the growth of transplanted mouse tumors as established by the following test:

Lymphocytic leukemia P388 test

The animals used are $BDF_1$ mice all of one sex, weighing a minimum of 18 g and all within a 3 gram weight range. There are 5 or 6 animals per test group. The tumor transplant is by intraperitoneal injection of 0.5 ml of dilute ascitic fluid containing $10^6$ cells of lymphocytic leukemia P 388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg/kg injection. The results of this test with representative compounds of the present invention appear in Table II below. The criterion for efficacy is $T/C \times 100 \geq 125\%$.

TABLE II

| Lymphocytic Leukemia P388 Test | | | |
|---|---|---|---|
| Compound | Dose (mg/kg) | Median Survival (Days) | T/C × 100 (Percent) |
| Bis(2-imidazolin-2-ylhydrazone) of 9,10-anthracene- dicarboxaldehyde, dichloride, bis(platinum chloride chelate) | 50 | 29.5 | 268 |
| | 37.5 | 22.0 | 200 |
| | 25 | 22.5 | 205 |
| | 12.5 | 21.5 | 195 |
| | 6.25 | 20.5 | 186 |
| Control | 0 | 11.0 | — |
| 5-Fluorouracil | 60 | 21.5 | 195 |
| Bis(2-imidazolin-2-ylhydrazone) of 9,10-anthracene- dicarboxaldehyde, dichloride, bis(cuprous chloride chelate) | 12.5 | 21.5 | 215 |
| | 6.25 | 19.5 | 195 |
| | 3.12 | 19.0 | 190 |
| | 1.56 | 18.5 | 185 |
| Control | 0 | 10.0 | — |
| 5-Fluorouracil | 60 | 21.0 | 210 |
| Bis(2-imidazolin-2-ylhydrazone) of 9,10-anthracene- dicarboxaldehyde, dichloride, bis(ferrous chloride chelate) | 12.5 | 24.0 | 240 |
| | 6.25 | 19.0 | 190 |
| | 3.12 | 20.0 | 200 |
| | 1.56 | 18.5 | 185 |
| Control | 0 | 10.0 | — |
| 5-Fluorouracil | 60 | 21.0 | 210 |
| Bis(2-imidazolin-2-ylhydrazone) of 9,10-anthracene- dicarboxaldehyde, tetrachloride, bis(dicyclopentadienyl zirconium chelate) | 25 | 28.0 | 311 |
| | 12.5 | 22.0 | 244 |
| | 6.25 | 20.5 | 228 |
| | 3.12 | 17.5 | 194 |
| | 1.56 | 17.0 | 189 |
| Control | 0 | 9.0 | — |
| 5-Fluorouracil | 60 | 20.0 | 222 |
| Bis(2-imidazolin-2-ylhydrazone) of 9,10-anthracene- dicarboxaldehyde, dinitrate, bis(cobaltic nitrate chelate) | 25 | 24.0 | 267 |
| | 12.5 | 21.0 | 233 |
| | 6.25 | 19.0 | 211 |
| | 3.12 | 18.5 | 206 |
| | 1.56 | 19.0 | 211 |
| Control | 0 | 9.0 | — |
| 5-Fluorouracil | 60 | 20.0 | 222 |
| Bis(2-imidazolin-2-ylhydrazone) of 9,10-anthracene- dicarboxaldehyde, tetrachloride, bis(chromic chloride chelate) | 25 | 23.0 | 256 |
| | 12.5 | 22.0 | 244 |
| | 6.25 | 19.0 | 211 |
| | 3.12 | 19.0 | 211 |
| | 1.56 | 18.0 | 200 |
| Control | 0 | 9.0 | — |
| 5-Fluorouracil | 60 | 20.0 | 222 |

The novel chelated compounds of formula (I) and their nontoxic pharmaceutically acceptable acid-addition and quaternary ammonium salts are expected to show activity against a broad range of cancer diseases, and especially blood cancer diseases such as leukemia, in standard test animals at doses substantially below toxic levels.

The modes contemplated for administration of the active chelated compounds are essentially parenteral and intraperitoneal. Solutions of the active compound as a free base or a pharmaceutically acceptable salt can be prepared in water, or in water suitably mixed with a surfactant such as, for example, hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by using agents in the compositions delaying absorption, for example, aluminum monostearate and gelatin.

Sterile injectable solutions are prepared by incorporating the active compound in the required amount in the appropriate solvent with various other above-enumerated ingredients, as required, followed by filtered sterilization. Generally, dispersions are prepared by incorporating the various sterilized active ingredient into a sterile vehicle that contains the basic dispersion medium and the required other ingredients from those enumerated above. In the case of sterile powders for the preparation of sterile injectable solutions, the preferred methods of preparation are the vacuum drying and the freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional medium or agent is incompatable with the active ingredient, its use in the present compositions is contemplated. Supplementary active ingredients can also be incorporated into the compositions.

It is especially advantageous to formulate compositions in dosage unit form for ease of administration and uniformity of dosage. "Dosage unit form" as used in the specification herein refers to physically discrete units suited as unitary dosages for the warmblooded animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The dosage of the principal active ingredient for the treatment of the indicated conditions depends upon the age, weight and condition of the subject being treated; the particular condition and its severity; the particular form of the active ingredient and the route of administration. A daily dose of from about one to about 100 mg/kg of body weight given singly or in divided doses of up to 5 times a day embraces the effective range for the treatment of most conditions for which the novel compounds are effective and substantially nontoxic. For a 75-kg subject, this translates into between about 75 and about 7500 mg per day. If the dosage is divided, for example, into 3 individual dosages, these will range from about 25 to about 2500 mg of the active ingredient. The preferred range is from 2 to about 50 mg/kg of body weight per day with about 2 to about 30 mg/kg per day being more preferred.

The principal active ingredient is compounded for convenient and effective administration in effective amounts with a suitable pharmaceutically acceptable carrier in dosage unit form as hereinbefore disclosed. A unit dosage form can, for example, contain the principal active ingredient in amounts ranging from about 0.1 to about 400 mg, with from about one to 30 mg being preferred. Expressed in proportions, the active ingredient is generally present in from about 0.1 to about 400 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administrated is a sufficient amount to aid regression and palliation of the leukemia or the like, in the absence of excessive deleterious side effects of a cytotoxic nature to the hosts harboring the cancer. As used herein, cancer means blood malignancies such as leukemia, as well as other solid and nonsolid malignancies such as the melanocarcinomas, lung carcinomas and mammary tumors. By regression and palliation is meant arresting or retarding the growth of the tumor or other manifestation of the disease compared to the course of the disease in the absence of treatment.

The novel chelated compounds of the present invention may be readily prepared from the compounds of U.S. Pat. No. 4,258,181. Using the latter compounds as starting materials, the metal chelates of the present invention are prepared by dissolving the appropriate anthracene-9,10-bis-carbonylhydrazone in a solvent such as methanol, making basic with, for example, potassium hydroxide, refluxing with one or more molar equivalents of a metal salt such as, for example, zirconocene dichloride, for from one to ten hours and recovering the desired metal chelate by conventional means.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims. Starting materials for the following examples are fully set forth in U.S. Pat. No. 4,258,181 that is hereby incorporated by reference.

A further understanding of the invention can be obtained from the following non-limiting Preparations and Examples.

EXAMPLE 1

Bis(2-imidazolin-2-ylhydrazone) of 9,10-anthracenedicarboxaldeyde, tetrachloride, bis(dicyclopentadienyl zirconium chelate)

A suspension of 5.0 g of 9,10-anthracenedicarboxaldehyde and 7.8 g of 2-hydrazino-2-imidazoline dihydrochloride in 75 ml of n-propanol is refluxed for 2 hours. The mixture is cooled and the solid is collected giving bis(2-imidazolin-2-ylhydrazone) of 9,10-anthracenedicarboxaldehyde, dihydrochloride.

A mixture of 1.0 g of bis(2-imidazolin-2-ylhydrazone) of 9,10-anthracenedicarboxaldehyde, dihydrochloride, 230 mg of potassium hydroxide and 1.2 g of zirconocene dichloride in methanol is refluxed for 5 hours, cooled and then filtered, giving 1.3 g of the desired product as an orange-brown solid.

EXAMPLE 2

Bis(2-imidazolin-2-ylhydrazone) of 9,10-anthracenedicarboxaldehyde, dinitrate, bis(cobaltic nitrate chelate)

A mixture of 1.0 g of bis(2-imidazolin-2-ylhydrazone) of 9,10-anthracenedicarboxaldehyde, dihydrochloride, 230 mg of potassium hydroxide and 1.2 g of cobalt nitrate hexahydrate in methanol is refluxed for 6 hours, cooled and then filtered, giving 600 mg of the desired product as a yellow-green solid.

EXAMPLE 3

Bis(2-imidazolin-2-ylhydrazone) of 9,10-anthracenedicarboxaldehyde, tetrachloride, bis(chromic chloride chelate)

A mixture of 1.0 g of bis(2-imidazolin-2-ylhydrazone) of 9,10-anthracenedicarboxaldehyde, dihydrochloride, 230 mg of potassium hydroxide and 1.08 g of chromium trichloride hexahydrate in methanol is refluxed for 6 hours, cooled and filtered, giving 1.3 g of the desired product as a red-brown solid.

EXAMPLE 4

Bis(2-imidazolin-2-ylhydrazone) of 9,10-anthracenedicarboxaldehyde, trisulfate, tris(zinc sulfate chelate)

A mixture of 1.0 g of bis(2-imidazolin-2-ylhydrazone) of 9,10-anthracenedicarboxaldehyde, dihydrochloride, 230 mg of potassium hydroxide and 1.15 g of zinc sulfate septahydrate in methanol is refluxed for several hours, cooled and filtered, giving 200 mg of the desired product, m.p. 325°–327° C. (dec.).

EXAMPLE 5

Bis(2-imidazolin-2-ylhydrazone) of 9,10-anthracenedicarboxaldehyde, dichloride, bis(platinum chloride chelate)

A mixture of bis(2-imidazolin-2-ylhydrazone) of 9,10-anthracenedicarboxaldehyde, dihydrochloride, potassium hydroxide and platinum chloride in methanol is reacted as described in Example 1, giving 500 mg of the desired product as an orange solid.

EXAMPLE 6

Bis(2-imidazolin-2-ylhydrazone) of 9,10-anthracenedicarboxaldehyde, dichloride, bis(cuprous chloride chelate A mixture of bis(2-imidazolin-2-ylhydrazone) of 9,10-anthracenedicarboxaldehyde, dihydrochloride, potassium hydroxide and cuprous chloride in methanol is reacted as described in Example 1, giving 500 mg of the desired product as a green solid.

EXAMPLE 7

Bis(2-imidazolin-2-ylhydrazone) of 9,10-anthracenedicarboxaldehyde, dichloride, bis(ferrous chloride chelate)

A mixture of bis(2-imidazolin-2-ylhydrazone) of 9,10-anthracenedicarboxaldehyde, dihydrochloride, potassium hydroxide and ferrous chloride in methanol is reacted as described in Example 1, giving 500 mg of the desired product as a green solid.

EXAMPLES 8–62

By carrying out the procedures of examples 1–7, metal chelates are formed from the following compounds as set forth in Table III.

TABLE III

| Example | Compound |
| --- | --- |
| 8 | Bis(dimethylhydrazone) of 9,10-anthracenedicarboxaldehyde dihydrochloride |
| 9 | N,N—Dimethylglycine(9,10-anthrylenedimethylidyne)-dihydrazine dihydrochloride |
| 10 | 1,1'-[9,10-Anthrylenebis(methylidynenitrilo)]diguanidine dihydrochloride |
| 11 | Bis(1,4,5,6-tetrahydro-2-pyrimidinylhydrazone) of 9,10-anthracenedicarboxaldehyde dihydrochloride |
| 12 | Bis(4,5,6,7-tetrahydro-1H—1,3-diazepin-2-ylhydrazone) of 9,10-anthracenedicarboxaldehyde dihydroiodide |
| 13 | 1,1'-[9,10-Anthrylenebis(methylidynenitrilo)]bis-3-benzylguanidine dihydroiodide |
| 14 | 1,1'-[9,10-Anthrylenebis(methylidynenitrilo)]bis(3-cyclohexylguanidine)dihydroiodide |
| 15 | Bis(2-imidazolin-2-ylmethylhydrazone) of 9,10-anthracenedicarboxaldehyde dihydroiodide |
| 16 | 1,1'-[9,10-Anthrylenebis(methylidynenitrilo)]bis-3-methylguanidine dihydroiodide |
| 17 | 9,10-Anthracenedicarboxaldehyde bis(thiosemicarbazone) |
| 18 | 9,10-Anthracenedicarboxaldehyde disemicarbazone |
| 19 | 1,1'-(9,10-Anthrylenedimethylidyne)bis-3-thiocarbohydrazide |
| 20 | 3,3'-[9,10-Anthrylenebis(methylidynenitrilo)]bis thiocarbazimidic acid dimethyl ester dihyroiodide |
| 21 | 9,10-Anthracenedicarboxaldehyde bis(methylhydrazone) |
| 22 | 1,1'-[9,10-Anthrylenebis(methylidynenitrilo)]bis-1-methylguanidine dihydrobromide |
| 23 | 1,1'-[9,10-Anthrylenebis)methylidynenitrilo)]bis[3,3-dimethyl-guanidine] dihydroiodide |
| 24 | 1,1'-[9,10-Anthrylenebis(methylidynenitrilo)]bis[1,3-dimethyl-guanidine]dihydroiodide |
| 25 | 1,1'-[Anthrylenebis(methylidynenitrilo)]bis[3-(2-hydroxyethyl)guanidine] dihydroiodide |

TABLE III-continued

| Example | Compound |
|---------|----------|
| 26 | 1,1'-[9,10-Anthrylenebis(methylidynenitrilo)]bis[3-(2-hydroxy-propyl)guanidine dihydroiodide |
| 27 | Bis(5-hydroxy-3,4,5,6-tetrahydropyrimidin-2-yl hydrazone) of 9,10-anthracenedicarboxaldehyde dihydrobromide |
| 28 | 1,1'-[9,10-Anthrylenebis(methylidynenitrilo)]bis[3-(3-dimethylaminopropyl)-2-ethylguanidine] tetrahydrochloride |
| 29 | 1,1'-[9,10-Anthrylenebis(methylidynenitrilo)]bisbiguanide tetrahydrochloride |
| 30 | 9,10-Anthracenedicarboxaldehyde bis (2-pyridylhydrazone) |
| 31 | 9,10-Anthracenedicarboxaldehyde bis[(2-dimethylaminoethyl)hydrazone] |
| 32 | N,N''-[9,10-Anthrylenebis(methylidynenitrilo)]-diacetamide dihydrochloride |
| 33 | Dibutyl 3,3'-(9,10-Anthrylenedimethylidyne)bis[thiocarbazimidate dihydroiodide] |
| 34 | Dibenzyl 3,3'-(9,10-Anthrylenedimethylidyne)bis[thiocarboximidate dihydrochloride] |
| 35 | 9,10-Anthracenedicarboxaldehyde bis(4,4-dimethylthiosemicarbazone) |
| 36 | Bis(2-imidazolin-2-ylhydrazone) of 9,10-anthracenediacetaldehyde dihydrochloride |
| 37 | 1,1'-[2-Methyl-9,10-anthrylenebis(methylidynenitrilo)]-diguanidine dihydrochloride |
| 38 | 1,1'-[2,3,6,7-tetramethoxy-9,10-anthrylenebis)methylidynenitrilo)]diguanidine dihydrochloride |
| 39 | 1,1'-[Ethyl-9,10-anthrylenebis(methylidynenitrilo)]-diguanidine dihydrochloride |
| 40 | [Bis(2-imidazolin-2-ylhydrazone)] of 2-chloro-9,10-anthracenedicarboxaldehyde dihydrochloride |
| 41 | 1,1'-[2-Nitro-9,10-anthrylenebis(methylidynenitrilo)]-diguanidine dihydrochloride |
| 42 | Bis(2-imidazolin-2-ylhydrazone) of 2-hydroxy-9,10-anthracenedicarboxaldehyde dihydrochloride |
| 43 | 1,1'-[9,10-Anthrylenebis(methylidynenitrilo)]bis[3-furfurylguanidine] dihydrochloride |
| 44 | 1,1'-[9,10-Anthrylenebis(methylidynenitrilo)]bis[3-(2-thenyl)guanidine]dihydrochloride |
| 45 | 1,1'-[9,10-Anthrylenebis(methylidynenitrilo)]bis[2,3-diisopropylguanidine]dihydroiodide |
| 46 | Bis(2-imidazolin-2-ylhydrazone) of 2-methyl-9,10-Anthracenedicarboxaldehyde dihydrochloride monohydrate |
| 47 | Bis(2-imidazolin-2-ylhydrazone) of 2,6-difluoro-9,10-anthracenedicarboxaldehyde |
| 48 | Bis(2-imidazolin-2-ylhydrazone) of 2,3-dimethyl-9,10-anthracenedicarboxaldehyde |
| 49 | Bis(2-imidazolin-2-ylhydrazone) of 2,6-dichloro-9,10-anthracenedicarboxaldehyde dihydrochloride |
| 50 | Bis(2-imidazolin-2-ylhydrazone) of 1,4-dimethyl-9,10-anthracenedicarboxaldehyde dihydrochloride |
| 51 | Bis(2-imidazolin-2-ylhydrazone) of 1,5-difluoro-9,10-anthracenedicarboxaldehyde, dihydrochloride |
| 52 | Bis(2-imidazolin-2-ylhydrazone) of fluoro-9,10-anthracenedicarboxaldehyde, dihydrochloride |
| 53 | Bis(2-imidazolin-2-ylhydrazone) of 1-fluoro-9,10-anthracenedicarboxaldehyde, dihydrochloride |
| 54 | Bis(2-imidazolin-2-ylhydrazone) of 1-chloro-9,10-anthracenedicarboxaldehyde, dihydrochloride |
| 55 | Bis(2-imidazolin-2-ylhydrazone) of 1-chloro-2-methyl-9,10-anthracenedicarboxaldehyde, dihydrochloride |
| 56 | 1,1'-[2-Chloro-9,10-anthrylenebis(methylidynenitrilo)]-bis[3,3-dimethylguanidine] dihydroiodide |
| 57 | Bis(1,4,5,6,-tetrahydro-2-pyrimidinylhydrazone) of 2-chloro-9,10-anthracenedicarboxaldehyde, dihydrochloride |
| 58 | Bis(2-imidazolin-2-ylhydrazone) of 2-ethyl-9,10-anthracenedicarboxaldehyde, dihydrochloride |
| 59 | 1,1'-[2-Chloro-9,10-anthrylenebis(methylidynenitrilo)]-diguanidine, dihydrochloride |
| 60 | 9,10-Anthracenedicarboxaldehyde,bis(4,5,6,7-tetrahydro-3H—azepin-2-ylhydrazone) dihydrochloride |
| 61 | 1,1'-[9,10-Anthrylenebis(methylidynenitrilo)]bis[3-(2-dimethylaminoethyl)guanidine]tetrahydrochloride |
| 62 | 9,10-Anthracenedicarboxaldehyde, bis [4-(3-dimethylaminopropyl)-3-thiosemicarbazone] dihydrochloride |

We claim:

1. A chelated compound selected from the group consisting of those of the formula:

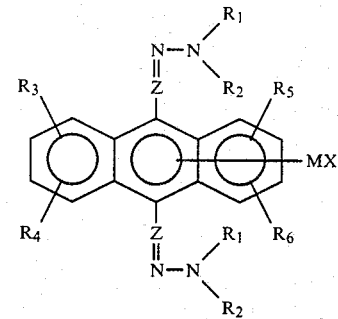

wherein Z is a trivalent moiety of the formulae:

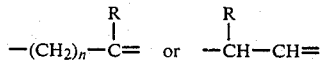

wherein n is 0, 1, 2, or 3 and R is hydrogen or alkyl ($C_1$–$C_4$); $R_1$ is hydrogen or alkyl ($C_1$–$C_4$); $R_2$ is hydrogen, alkyl ($C_1$–$C_4$) or a monovalent moiety of the formulae:

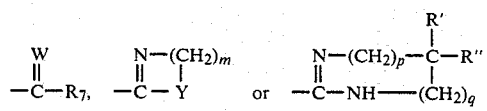

wherein m is 2, 3, 4 or 5, p is 1, 2 or 3, q is 0, 1 or 2; R' is hydrogen or alkyl ($C_1$–$C_4$); R" is hydrogen or alkyl ($C_1$–$C_4$); $R_7$ is alkyl ($C_1$–$C_4$), amino, anilino, hydrazino, alkylamino ($C_1$–$C_4$), dialkylamino wherein each alkyl group has up to 4 carbon atoms, α-phenethylamino, β-phenethylamino, pyrrolidino, piperidino, N-methylpiperazino or a moiety of the formula:

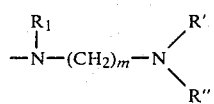

wherein m, $R_1$, $R'$ and $R''$ are as hereinbefore defined and the moiety $-NR'R''$ may be pyrrolidino, piperidino, morpholino or N-methylpiperazino; W is oxo (O=), thioxo (S=) or imino ($R'-N=$ wherein $R'$ is as hereinbefore defined) and Y is oxy (—O—), thio (—S—), or methylene (—$CH_2$—); and $R_3$, $R_4$, $R_5$ and $R_6$ are each individually selected from the group consisting of hydrogen, halogen (F, Cl, Br, I), hydroxy, nitro, amino, sulfonamido, alkyl ($C_1$–$C_3$) and alkoxy ($C_1$–$C_3$); M is platinum, copper, iron, zirconium, cobalt, chromium or zinc; X is sulfate, halogen (F, Cl, Br, I), nitrate, dicyclopentadienyl or amine ligand; and the nontoxic pharmaceutically acceptable acid-addition and quaternary ammonium salts thereof.

2. The compound according to claim 1, bis(2-imidazolin-2-ylhydrazone) of 9,10-anthracenedicarboxaldehyde, dichloride, bis(platinum chloride chelate).

3. The compound according to claim 1, bis(2-imidazolin-2-ylhydrazone) of 9,10-anthracenedicarboxaldehyde, dichloride, bis(cuprous chloride chelate).

4. The compound according to claim 1, bis(2-imidazolin-2-ylhydrazone) of 9,10-anthracenedicarboxaldehyde, dichloride, bis(ferrous chloride chelate).

5. The compound according to claim 1, bis(2-imidazolin-2-ylhydrazone) of 9,10-anthracenedicarboxaldehyde, tetrachloride, bis(dicyclopentadienyl zirconium chelate).

6. The compound according to claim 1, bis(2-imidazolin-2-ylhydrazone) of 9,10-anthracenedicarboxaldehyde, dinitrate, bis(cobaltic nitrate chelate).

7. The compound according to claim 1, bis(2-imidazolin-2-ylhydrazone) of 9,10-anthracenedicarboxaldehyde, tetrachloride, bis(chromic chloride chelate).

8. The compound according to claim 1, bis(2-imidazolin-2-ylhydrazone) of 9,10-anthracenedicarboxaldehyde, trisulfate, tris(zinc sulfate chelate).

* * * * *